United States Patent
Heckenberger et al.

(10) Patent No.: US 8,974,745 B2
(45) Date of Patent: Mar. 10, 2015

(54) DEVICE FOR DISINFECTING, STERILIZING AND/OR MAINTAINING MEDICAL, ESPECIALLY DENTAL, INSTRUMENTS

(75) Inventors: Hans Heckenberger, Assmannshardt (DE); Hans-Dieter Wiek, Hochdorf (DE)

(73) Assignee: Kaltenbach & Voigt GmbH, Biberach (DE)

( * ) Notice: Subject to any disclaimer, the term of this patent is extended or adjusted under 35 U.S.C. 154(b) by 0 days.

(21) Appl. No.: 13/522,926

(22) PCT Filed: Jan. 27, 2011

(86) PCT No.: PCT/EP2011/051121
§ 371 (c)(1),
(2), (4) Date: Aug. 8, 2012

(87) PCT Pub. No.: WO2011/101214
PCT Pub. Date: Aug. 25, 2011

(65) Prior Publication Data
US 2012/0301369 A1    Nov. 29, 2012

(30) Foreign Application Priority Data
Feb. 17, 2010  (DE) .......................... 10 2010 002 027

(51) Int. Cl.
*A61L 2/16*  (2006.01)
*A61L 2/07*  (2006.01)
*A61C 19/00* (2006.01)
*A61L 2/24*  (2006.01)

(52) U.S. Cl.
CPC ................. *A61L 2/07* (2013.01); *A61C 19/002* (2013.01); *A61L 2/24* (2013.01); *A61L 2202/24* (2013.01)
USPC .......................................................... 422/300

(58) Field of Classification Search
USPC .................................................... 422/300, 28
See application file for complete search history.

(56) References Cited

U.S. PATENT DOCUMENTS

| 4,846,221 A | * | 7/1989 | Kanemaru ............... 137/614.17 |
| 4,934,651 A | * | 6/1990 | Nowicki ......................... 251/54 |
| 5,723,090 A |   | 3/1998 | Beerstecher et al. |

(Continued)

FOREIGN PATENT DOCUMENTS

| DE | 20017039 U1 | 1/2001 |
| EP | 0 638 297 A1 | 2/1995 |

(Continued)

OTHER PUBLICATIONS

Dura Magnets, Inc. "Ceramic Magnets". retrieved from a capture by the Internet Archive Wayback Machine from Dec. 9, 2009.*

(Continued)

*Primary Examiner* — Sean E Conley
*Assistant Examiner* — Donald Spamer
(74) *Attorney, Agent, or Firm* — Marshall, Gerstein & Borun LLP

(57) ABSTRACT

A conditioning device for disinfecting, sterilizing and/or maintaining medical, especially dental, instruments comprises a distributor unit for supplying cleaning or maintenance media to the instruments, said distributor unit having respective inlets for every medium, said inlet being connected to a support for an instrument via a valve. Every valve comprises a sealing element which can be brought into a valve-opening position by means of the actuating element of the distributor unit which can be selectively positioned.

6 Claims, 2 Drawing Sheets

(56) References Cited

U.S. PATENT DOCUMENTS

| | | | |
|---|---|---|---|
| 2005/0084414 A1* | 4/2005 | Treiman | 422/28 |
| 2007/0031778 A1* | 2/2007 | Helfenbein et al. | 433/82 |
| 2008/0083892 A1* | 4/2008 | Fenton | 251/68 |
| 2012/0058014 A1 | 3/2012 | Heckenberger et al. | |

FOREIGN PATENT DOCUMENTS

| | | |
|---|---|---|
| EP | 1749502 A1 | 2/2007 |
| WO | WO-2010106161 A2 | 9/2010 |

OTHER PUBLICATIONS

Kenyon College Physics. "The Electromagnet". retrieved from a capture by the Internet Archive Wayback Machine from Dec. 2, 2009.*

International Search Report for PCT/EP2011/051121 dated Apr. 12, 2011.

* cited by examiner

DEVICE FOR DISINFECTING, STERILIZING AND/OR MAINTAINING MEDICAL, ESPECIALLY DENTAL, INSTRUMENTS

BACKGROUND OF THE INVENTION

1. Field of the Invention

The present invention relates to a device which is provided for disinfecting, sterilizing and/or maintaining medical instruments. In particular, dental instruments are to be conditioned with the device.

2. Related Technology

Medical or dental handpieces are tubular parts which the doctor holds as a handle during treatment. A handpiece conventionally used in dental practice is a so-called drill handpiece, which carries a treatment tool, in particular a drill, at its forward end and is coupled at its rear end to a supply hose by means of a coupling. Supply lines for power for driving the treatment instrument, as well as fluid lines for treatment media, for example air and/or water, extend through the handpiece. A distinction is often made between so-called turbine handpieces, in which compressed air is provided for supplying a turbine arranged in the forward end region, and so-called motor handpieces, which have an electric motor as the drive unit.

In order to maintain the function of the handpieces, maintenance, in particular of the rotatably mounted drive elements, is required from time to time. Furthermore, ever increasing hygiene demands in dental practice mean that handpieces have to be conditioned at regular intervals. Successful conditioning and compliance with the corresponding requirements must be fully documented by the dentist, which involves a not inconsiderable outlay in terms of personnel and organization.

Manual reconditioning of dental handpieces has hitherto been carried out by first disinfecting the instruments by spraying and washing them externally after use on a patient. Cleaning of the interior of the instruments, on the other hand, was generally not carried out. In the meantime, however, cleaning and disinfecting devices in which the instruments are conditioned before being subjected to maintenance with oil have become available on the market. Machine conditioning has clear advantages over manual maintenance of the instruments, because only a machine process permits reliable and reproducible cleaning and maintenance.

However, the devices known hitherto can generally be used only for individual conditioning steps, so that cleaning, maintenance and sterilization must each be carried out separately. All the devices required therefor take up a relatively large amount of space, and electrical, pneumatic and fluid connections are required for each of the devices. Consequently, the performance of a complete machine conditioning of dental instruments by means of individual devices is very laborious and is associated with a high outlay in terms of cost.

A further disadvantage is that the individual devices are generally not linked with one another, so that there can be no exchange of data between the devices. This in turn leads to extra work for the operating personnel, because it is not possible to prepare fully automatic documentation of instrument conditioning. Furthermore, the instruments must be moved manually from device to device in intermediate steps, which is associated with intensive personnel use and a large time requirement.

For the reasons mentioned above, increasing use has recently been made of devices or systems which allow complete conditioning of a dental instrument. Such devices carry out different measures in succession in order to condition the instruments, for which they make use of very different media. For example, cleaning agents, disinfectants and maintenance and compressed air are used in order to achieve complete reconditioning of the instruments. This necessarily requires the presence of a system for distributing and making available very different media.

Solutions known hitherto are based on the distribution of the individual media to the instruments by corresponding solenoid valve blocks. Such a solution is associated with a comparatively high outlay and consequently also with corresponding costs.

SUMMARY OF THE INVENTION

The object underlying the present invention is, therefore, to provide an inexpensive alternative for supplying different media.

The object is achieved by a reconditioning device for disinfecting, sterilizing and/or maintaining medical, especially dental, instruments.

The solution according to the invention is based on the use of a novel distributor unit which has specially configured valves which are inexpensive to produce. To that end, it is provided that each valve has a sealing element which can be brought into a valve-opening position by a selectively positionable actuating element of the distributor unit.

Accordingly, there is proposed according to the present invention a reconditioning device for disinfecting, sterilizing and/or maintaining medical, especially dental, instruments which has a distributor unit for supplying cleaning or maintenance media to the instruments, wherein the distributor unit has for each medium a central inlet which is connected via a valve to a support for an instrument, and wherein each valve has a sealing element which can be brought into a valve-opening position by a selectively positionable actuating element of the distributor unit.

The actuating element is preferably arranged on a slider which can be, for example, movable linearly or rotatable. The actuating element can be configured to actuate directly the sealing element of the valve that is to be controlled. Alternatively, however, it can be provided that the sealing element of a valve is made of a ferritic material and the actuating element is formed by a magnet, in particular by an electromagnet.

The sealing element in turn can be formed by a plunger or by a plate.

Ultimately, the solution according to the invention creates an arrangement with which the different media can be passed in a simple and convenient manner to the instruments that are to be conditioned. This arrangement is inexpensive to produce but nevertheless has high operational reliability.

BRIEF DESCRIPTION OF THE DRAWINGS

The invention is to be explained in greater detail below by means of the accompanying drawings, in which.

DETAILED DESCRIPTION

Figure 1:
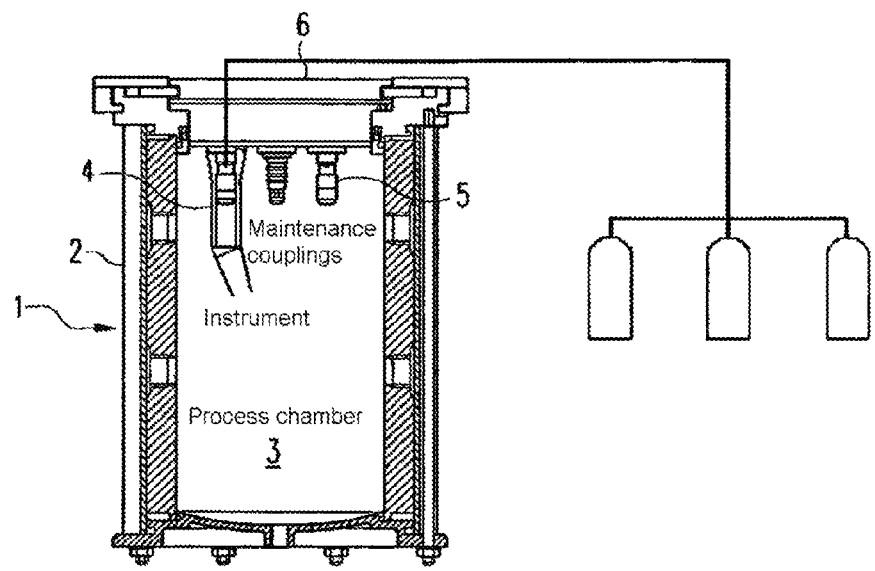
FIG. 1 shows, in a sectional view, a process or rinsing chamber of a device for disinfecting, sterilizing and/or maintaining dental instruments.

FIG. 1 first shows, in schematic form, the configuration of a device for disinfecting, sterilizing and/or maintaining medical, especially dental, instruments, the device being provided generally with the reference numeral 1 hereinbelow. The central element of the maintenance device 1 according to the invention is a pressure container 2, which encloses a process or rinsing chamber 3. The instruments 4 to be cleaned or maintained are arranged in this rinsing chamber 3 while the process is being carried out. The arrangement of the instruments 4 is effected by means of an instrument carrier, on which several plug-in positions or couplings 5 are arranged. Different couplings 5 are preferably provided, so that instruments 4 with coupling systems from different manufacturers can be conditioned. In the present case, the lid 6 of the process chamber 3 is used as the instrument carrier. This lid 6 provides the fluid coupling of the instruments 4 that are to be cleaned to a supply system. It is clamped on the rim of the pressure container 2 and sealed with respect thereto by a locking device. The individual instruments 4 and their channels can then be subjected, individually or together, to a cleaning and/or maintenance agent via connecting pipes integrated into the lid 6.

The process sequence in the case of the cleaning and/or maintenance of the instruments 4 is first to be described generally hereinbelow. Before the start of the conditioning, it is checked that the process chamber 3 is pressure-tight. It is thereby ensured that the lid 6 is fitted correctly and is locked with the pressure container 2. A check is also made to ensure correct connection of the fluid lines between the lid 6 and lines running in the rim of the pressure container 2.

For the water supply to the device 1, tap water is preferably filtered by means of an osmosis system with or without downstream mixed-bed ion exchangers, the dissolved salts being removed. The water, with a quality of <15 µS/cm, is passed into a storage container on the device side, the filling level being monitored by a level switch, which is in the form of a floating switch, and the quality being monitored via a conductance sensor. For hygiene reasons, the inlet into the storage container is configured with a so-called free-fall distance.

In the conditioning of the instruments by means of the device according to the invention, the following steps are then executed in succession:

a) Cleaning

Water is first passed from the above-described storage container into the process chamber 3, it being possible for this operation to be carried out by a pump or via a vacuum by suction. In the process chamber 3, the water is heated to about 45° C. by means of heating elements. Here it is ensured that the temperature is not above 45° C. in order to prevent the coagulation of albumin. The water is further circulated by means of a pump and directed via spray nozzles, which are attached to the lateral surface of the pressure container 2 or in a central dome, onto the external surfaces of the instruments 4 in order to clean them. The cleaning water can here be passed through the instruments 4 and/or the spray channels of the instruments 4 and/or, for external cleaning, through the spray nozzles of the process chamber 3.

Heating of the wash medium can take place while it is being circulated, so that the surfaces to be cleaned are first cleaned with cold wash medium. The cleaning agent can be introduced into the process chamber 3 in the form of powder or in tablet form or it can be metered in from a corresponding storage container. The wash medium can consist of surfactants or phosphates and have a pH value above 10. In order to complete the washing operation, the water is discharged from the pressure container 2.

b) Clear Rinsing—Neutralization

In a subsequent step, the water is then passed from the storage container into the process chamber 3 and heated to approximately from 45° C. to 60° C. During circulation of the water, clear rinse or neutralizer is metered in from a further storage container. Alternatively, owing to the higher temperature in comparison with step a), a second component of a cleaning tablet can also be dissolved. The liquid is in turn passed in parallel or with a time shift, that is to say intermittently, through the instruments 4 and the spray channels or is directed at the external surfaces of the instruments 4 via the spray nozzles. As clear rinse or neutralizer there are used in particular phosphoric acid esters having a pH value of from 3 to 5.

The liquid can again be discharged from the pressure container into the drainage system, or it remains in the container in order, in the subsequent maintenance operation, to take up excess maintenance agent emerging from the instruments 4 or in order briefly to rinse the oily external surfaces of the instruments with warm liquid. In this case, the liquid is not discharged until after the maintenance operation, and it may be expedient to subject the instruments 4 to compressed air in order to prevent the ingress of spray water into the interior of the instruments 4.

c) Maintenance

In a third step, maintenance agent is passed from a maintenance agent storage container into the interior of the instruments, so that the gears and bearings are lubricated. The maintenance agent can be injected in liquid form as oil or from a pressurized dispenser into a compressed air jet. It is also possible to foam the oil via the propellant contained in the pressurized dispenser and to fill the interior of the instruments with the oil/air foam. In this case, the air bubbles collapse comparatively quickly, so that the oil forms a uniform thin oil film in the whole of the instrument interior. As lubricants there are used biodegradable fatty acid ester oil/white oil mixtures.

d) Rinsing

After the maintenance operation described above, the instruments can be rinsed on the external surface with the clear rinse liquid that is still present in the container. Alternatively, fresh water is fed from the storage container to the process chamber 3 via a pump and is directed at the external surfaces of the instruments via the spray nozzles.

e) Sterilization—Prevacuum

In order to sterilize the instruments, fresh water is fed to the process chamber 3 from the storage container. In the process chamber 3, a vacuum device is connected for ventilation, the pressure inside the process chamber 3 being monitored or recorded.

By means of the vacuum device, the air is evacuated from the process chamber 3. The vacuum is reduced by heating the water to atmospheric pressure via heating elements. The process chamber 3 is then filled with steam, it being possible for this procedure to be repeated several times depending on the sterilization programme.

The volume of water evaporated off can be made up at each vacuum cycle or, as an alternative, all the water required for the steam generation can be introduced into the process chamber 3 right at the start of the sterilization cycle.

Alternatively to the generation of steam via heating elements located in the process chamber 3, steam for pressure equalization during ventilation or for sterilization can also be supplied from a steam pressure vessel located outside the process chamber 3.

f) Drying and Cooling

When sterilization is complete, the instruments 4 are dried by causing the steam in the process chamber 3 to condense. This is achieved by cooling the container wall or elements located in the container, for example by passing through them water taken from the storage container. The water can be supplied continuously or intermittently. When the cooling operation is complete, the water is discharged. Because the temperature inside the chamber 3 is then below 50° C., the lid 6 can be opened. The conditioning cycle for the instruments 4 is thereby completed.

It is apparent from the above description that fully automatic conditioning of dental instruments is possible with the device 1. Interventions by operating personnel are not required, so that the system is very convenient. Naturally, it is also possible to deviate from the described sequence for conditioning of the instruments. At the same time, it will be seen that very different agents and media can be used for the conditioning of the devices.

Consequently, as is shown in schematic form in FIG. 1, the device 1 is connected to different storage containers for different media, it being possible for the media located in the storage containers selectively to be removed and fed to the instruments. This is effected by an arrangement for distributing the various media, which was hitherto based primarily on the use of a plurality of solenoid valve blocks via which the media were distributed to the instruments. With the present invention, a novel arrangement for distributing the media is proposed, which can be produced more simply and inexpensively. This arrangement is to be explained below with reference to FIGS. 2 and 3.

Figure 2:
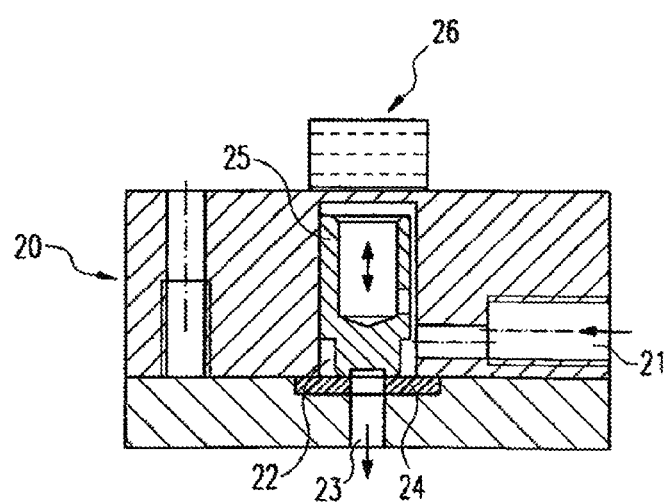
FIG. 2 shows an individual valve of an arrangement according to the invention for supplying media.

The arrangement according to the invention is based on specially configured valves, one of which is shown in FIG. 2. It has a medium inlet 21, which is connected via a chamber 22 with the outlet 23 of the valve 20. At the outlet there is a seal 24, which is sealed via a plunger 25. The plunger 25 can be moved into a position that opens or closes the valve 20, as desired.

Actuation of the plunger 25 is effected via an actuating element 26 which is arranged on the upper side of the valve and in the present case is formed by a magnet. As is explained in greater detail below, the magnet 26 can optionally be arranged on the upper side of a so-called distributor plate. If the magnet 26, which can be formed, for example, by an electromagnet, is located above the plunger 25, then the plunger 25—which is preferably made of a ferritic material—is attracted by the magnetic flux. It lifts off the seal 24 and thereby frees the path for the medium that is to be applied.

Figure 3:
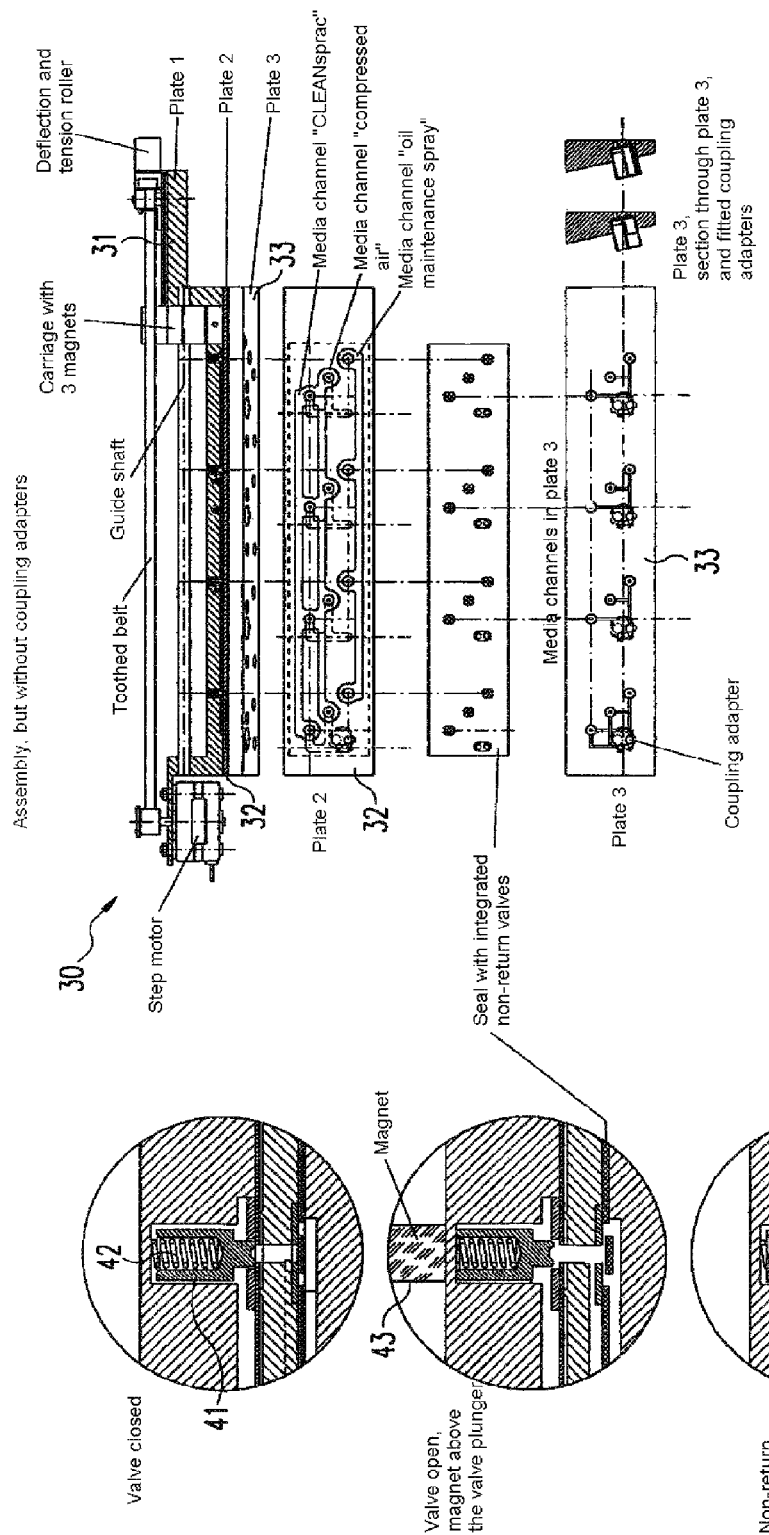
FIG. 3 shows, in schematic form, the configuration of an arrangement for supplying different media.

It is apparent from the above description that very simple control of the valve 20 is possible. This fundamental principle is then used to produce a larger arrangement for distributing the media, which is shown in FIG. 3. In the exemplary embodiment shown, this arrangement is to selectively supply three different media to the connection points for four dental instruments.

The arrangement 30 consists substantially of three plates arranged one above the other, the plungers of the various valves being arranged in the upper plate 31, the so-called distributor plate. In the second plate 32 located beneath it there are formed media channels, each of which branches from a central inlet, which is connected to the corresponding storage container, to four removal points. The seals mentioned above for the individual valves are then arranged beneath the media channels, the seals in the present case being configured with integrated non-return valves. Beneath the seals there is arranged the third plate, in which individual channels are again formed, which each lead from the valve openings to the associated coupling adapter for the instrument that is to be reconditioned.

Accordingly, the arrangement provides a total of twelve valves, via which the various media can selectively be fed to the instruments. The valves are always closed in the initial state, which is achieved by the plunger 41 in each case being pushed into the closed position by a resilient element, for example a spiral spring 42—as is shown on the left-hand side of FIG. 3. However, by the arrangement of a magnet 43 on the upper side of the plunger 41, the valve can selectively be opened. The positioning of the magnet 43 is here effected via a slider, which either can be moved linearly or is rotatable. The slider allows the magnet 43 for actuating the valve to be selectively arranged in the appropriate position and thereby free the path for the medium that is to be applied. If, on the other hand, the magnet 43 is removed again, the plunger 41 is pressed onto the seal again by the spring 42.

The sealing edge of the plunger 41 is so configured that it seals with a flat side. This has the advantage that the plunger 41 does not have to meet the centre of the sealing bore exactly. Furthermore, in the closed state, the non-return valve of the seal is activated, so that the medium is prevented from flowing back.

The solution according to the invention consequently opens up, in a simple manner, the possibility of freely applying different media for different instruments. It is advantageous that no mixing of the media occurs, because they are guided separately to the instrument. The system can readily be extended to additional instrument points or additional media. This is associated only with very low additional costs. Furthermore, assembly is rapid because no hoses are to be laid to the respective maintenance position. Instead, a central feed point for the medium in question can be used.

Finally, it is to be noted that, instead of the magnet control, it would also be possible to use an arrangement in which the plunger is actuated directly by the slider. In this case, however, additional sealing of the plunger would be required.

The invention claimed is:

1. Reconditioning device for disinfecting, sterilizing and/or maintaining medical instruments, the reconditioning device having a distributor unit for supplying at least first and second cleaning or maintenance media to the instruments wherein the distributor unit comprises:
   a first inlet for the first medium, the first inlet being connected via a first valve to at least one instrument support;
   a second inlet for the second medium, the second inlet being connected via a second valve to the at least one instrument support; and
   an actuator configured to move between a first position proximate to the first valve and a second position proximate to the second valve, the actuator further being configured to open the first valve when the actuator is in the first position and to open the second valve when the actuator is in the second position.

2. Reconditioning device according to claim 1, wherein the actuator is arranged on a slider.

3. Reconditioning device according to claim 1, wherein each of the first and second valves includes a sealing element comprising a magnetic material, and the actuating element comprising a magnet.

4. Reconditioning device according to claim 3, wherein the magnet is an electromagnet.

5. Reconditioning device according to claim 1, wherein the sealing element is formed by a plunger.

6. Reconditioning device according to claim 1, wherein the sealing element is formed by a plate.

* * * * *